(12) United States Patent
Tegg et al.

(10) Patent No.: US 10,283,887 B2
(45) Date of Patent: May 7, 2019

(54) HIGH CAPACITY CONNECTOR FOR MEDICAL DEVICES

(71) Applicant: St. Jude Medical, Cardiology Division, Inc., St. Paul, MN (US)

(72) Inventors: Troy Tegg, Elk River, MN (US); Gregory K. Olson, Elk River, MN (US); Derek Sutermeister, Ham Lake, MN (US); Nicholas Strom, Minneapolis, MN (US); David Kim, Maple Grove, MN (US); Michael C. Bednarek, Buffalo, MN (US); Dale Just, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/815,021

(22) Filed: Nov. 16, 2017

(65) Prior Publication Data

US 2018/0138619 A1    May 17, 2018

Related U.S. Application Data

(60) Provisional application No. 62/423,040, filed on Nov. 16, 2016.

(51) Int. Cl.
| | |
|---|---|
| *H01R 12/00* | (2006.01) |
| *H01R 13/02* | (2006.01) |
| *H01R 13/193* | (2006.01) |
| *H01R 29/00* | (2006.01) |
| *H01R 13/66* | (2006.01) |
| *H01R 12/59* | (2011.01) |
| *H01R 24/28* | (2011.01) |

(52) U.S. Cl.
CPC ......... *H01R 13/025* (2013.01); *H01R 13/193* (2013.01); *H01R 13/6658* (2013.01); *H01R 29/00* (2013.01); *A61B 2562/0209* (2013.01); *A61B 2562/225* (2013.01); *H01R 12/59* (2013.01); *H01R 24/28* (2013.01)

(58) Field of Classification Search
CPC ...................................................... H01R 12/59
See application file for complete search history.

(56) References Cited

U.S. PATENT DOCUMENTS

| | | | | |
|---|---|---|---|---|
| 5,248,261 A | * | 9/1993 | Conroy-Wass | ...... G01R 1/0416 439/65 |
| 6,533,588 B1 | * | 3/2003 | Woith | ...... H01R 13/24 439/289 |

(Continued)

OTHER PUBLICATIONS

International Search Report and Written Opinion of the International Searching Authority, PCT Appl. No. PCT/US2017/062031, dated Mar. 13, 2018.

*Primary Examiner* — Tho D Ta
(74) *Attorney, Agent, or Firm* — Dykema Gossett PLLC

(57) ABSTRACT

The present disclosure relates to a high capacity medical device connector utilizing flexible circuits. The use of flexible circuits allows for increased channel capacity for use with future designs and capabilities of medical devices. The assembly may include pre-mounted electrical components. The connector may be designed to connect two flexible circuits. The connector may also be designed to connect a flexible circuit with existing technology, such as a pin-to-socket connector.

17 Claims, 14 Drawing Sheets

(56) References Cited

U.S. PATENT DOCUMENTS

| | | | |
|---|---|---|---|
| 7,918,670 B2* | 4/2011 | Shmatovich | G01R 1/0416 439/67 |
| 2005/0009382 A1* | 1/2005 | Burmeister | H01R 4/5058 439/67 |
| 2007/0054519 A1 | 3/2007 | Lin et al. | |
| 2008/0309287 A1 | 12/2008 | Reed | |
| 2012/0202370 A1 | 8/2012 | Mulfinger et al. | |
| 2014/0011403 A1 | 1/2014 | Siev et al. | |
| 2014/0039302 A1 | 2/2014 | Miller et al. | |
| 2014/0273631 A1* | 9/2014 | Birchard | G06F 1/16 439/620.01 |

* cited by examiner ated, but the connector must be able to accommodate a larger number of channels, while maintaining the ability to connect a medical device and a cable securely, quickly, and easily.

The foregoing discussion is intended only to illustrate the present field and should not be taken as a disavowal of claim scope.

HIGH CAPACITY CONNECTOR FOR MEDICAL DEVICES

CROSS-REFERENCE TO RELATED APPLICATIONS

This application claims priority to U.S. provisional patent application No. 62/423,040 entitled "HIGH CAPACITY CONNECTOR FOR MEDICAL DEVICES", filed on Nov. 16, 2016, which is hereby incorporated by reference as though full set forth in its entirety.

BACKGROUND a. Field of the Invention

This disclosure relates to cable connectors for medical devices such as catheters. In particular, this disclosure relates to cable connectors utilizing flex circuitry to increase capacity.

b. Background Art

The connection of medical devices, such as electrophysiology catheters, to one or more medical diagnostic or treatment systems by one or more electrical cables is well known. Such medical systems may be, for example, mapping systems, imaging systems, navigation systems, ablation systems, etc., and the electrical cables may be used to transmit signals and/or power between the medical device and the medical systems. A cable connector is frequently employed to provide a secure, quick and easy way to attach and detach the connection between the medical device and the medical system. Such connectors are frequently incorporated into a handle of a medical device, with a male or female fitting in the handle and a corresponding female or male fitting on the connecting cable.

A common connector design uses a pin-to-socket connection. Isolation between the data channels in the cable is maintained through sizing and spacing of the pins. The number of data channels carried by the cable is thus in part dependent on the size of the pins in the connector and the overall size of the connector itself. Pins must also be rigid enough to maintain adequate performance of the connector which sets a lower limit on the size of the pins. Thus, in order to increase the number of data channels in pin-to-socket connectors, the size of the connector must increase to accommodate the increase in pins. This often requires an increase in the size of the handle in a medical device at its proximal end, which is not always desirable.

Advances in medical device technology are happening at a rapid pace. More and more devices having various different functions are available and the number of devices capable of performing multiple functions is increasing. The various different functions in the devices—such as ablation electrodes, ultrasound, radio frequency, etc.—have different control and data needs, often resulting in numerous different types of cables to be connected to each device. For multifunction devices, the desire to have only one cable connection per device requires the connector to accommodate all the necessary channels. There is a desire then to provide a cable connector for a medical device that can accommodate all the necessary electrical channels of multi-function devices and can be a universal connection for different devices regardless of the specific functions in the device. Further, it is desirable for a cable connector to have excess capacity to accommodate medical devices with even more or different functions than are presently known. Thus, there is a need for a connector that allows for increased capacity to

BRIEF SUMMARY

The instant disclosure relates to cable connectors for medical devices, such as catheters and more specifically connectors, configured to provide a universal connection having increased electrical channels to support current and future multi-function medical devices.

The cable connectors described herein utilize one or more flexible circuits that may include a high-density wiring interface and a high-density contact interface. The flexible circuits of this disclosure may also include any number of tabs increasing the number of available channels as great as the combination of tabs can individually allow. The flexible circuits of this disclosure may also include pre-mounted components.

An embodiment of this disclosure allows for the connection of two flexible circuits. Each flexible circuit of the embodiment has a corresponding high-density contact interface and one or more tabs with a high-density wiring interface. One of the flexible circuits has a wiring interface to connect with the cable. The other flexible circuit has a wiring interface to connect with the catheter.

Another embodiment includes flexible tabs that connect to a pin-to-socket connector allowing for increased capacity and connection at the pin connector or socket connector. Each tab includes a high-density wiring interface. The flexible circuit may include a portion having a high-density contact interface which has automated bonding pins to connect with a pin connector.

In addition to accommodating current and future connector and cable requirements, the present disclosure allows several other benefits. The disclosure allows the catheter to maintain its current handle and shield can design. The present invention improves manufacturability of connectors. Bonding of wiring is improved, decreasing scrap rates. The disclosure solves current issues from bonding to cup terminals, such as shorts, wire positioning issues, solder flow, solder pull, and excessive solder. The disclosure solves current solder and flux issues, such as reducing sources of noise by automated pre-tinning. The disclosure allows for partial automation for wire termination. The present invention reduces or maintains scrap cost, labor cost, and connector cost.

The foregoing and other aspects, features, details, utilities, and advantages of the present invention will be apparent from reading the following description and claims, and from reviewing the accompanying drawings.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

Figure 1:
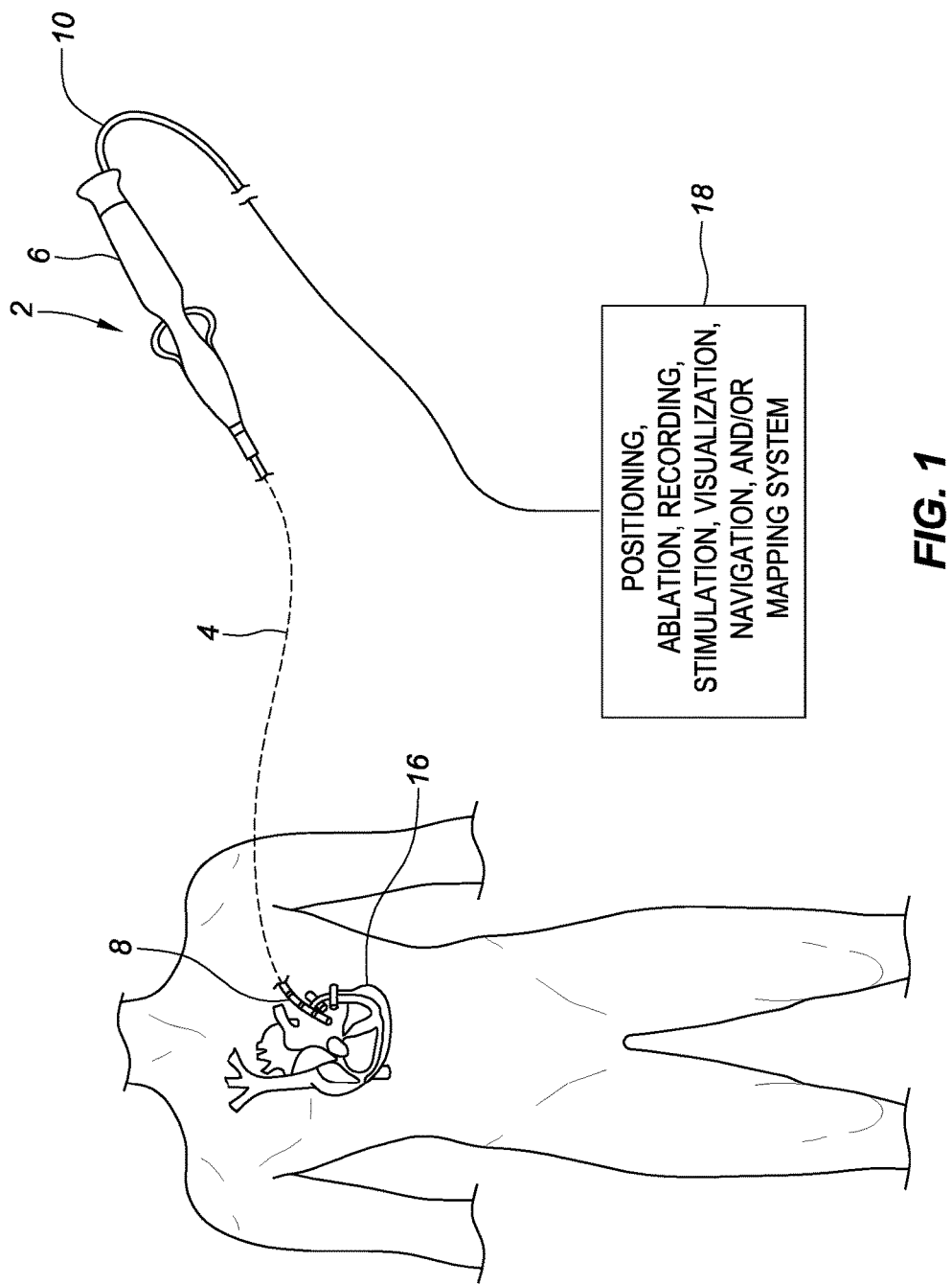
FIG. 1 is a diagrammatic view of a system for performing one or more diagnostic and/or therapeutic functions in association with cardiac tissue.

The disclosure herein relates to cable connectors for use with medical devices. One embodiment of an exemplary medical device is the mapping and ablation catheter 2 depicted in FIG. 1, which is part of a catheter system for examination, diagnosis, and/or treatment of internal tissues in a body. It should be understood that the present disclosure is applicable to other catheters, such as mapping catheters, imaging catheters, diagnostic catheters and therapeutic catheters, as well as any type of medical device utilizing cable connections.

The catheter 2 includes an elongate shaft 4 attached to a control handle 6 and configured for movement within a body 16. In some embodiments, the catheter 2 can further include one or more electrodes (not shown) mounted in or on the distal portion 8 of the elongate shaft 4. The electrodes can be used, for example, in operation with a positioning, ablation, recording, stimulation, visualization, navigation, and/or mapping system. The electrodes can be configured to provide a signal indicative of both a position and orientation of at least a portion of the elongate shaft 4. In some embodiments, the handle 6 can provide mechanical and electrical connection for a cable 10 extending to a medical device system 18, such as a positioning, ablation, recording, stimulation, visualization, navigation, and/or mapping system.

The handle 6 can provide a location for a clinician to hold the catheter 2 and can further provide means for steering or guiding the elongate shaft 4 within the body 16 as known in the art. Catheter handles are generally conventional in the art and it will be understood that the construction of the handle 6 can vary.

Figure 2A:
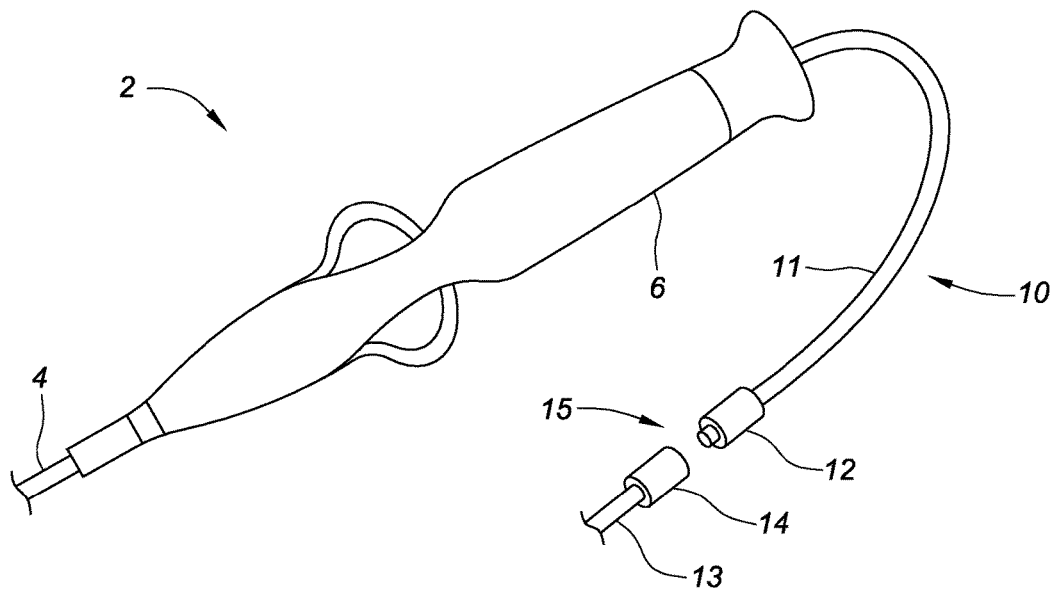
FIG. 2A generally illustrates a catheter including a control handle and an elongate shaft according to an exemplary use of a high capacity connector of the present invention having a cable connection external to the control handle.
Figure 2B:
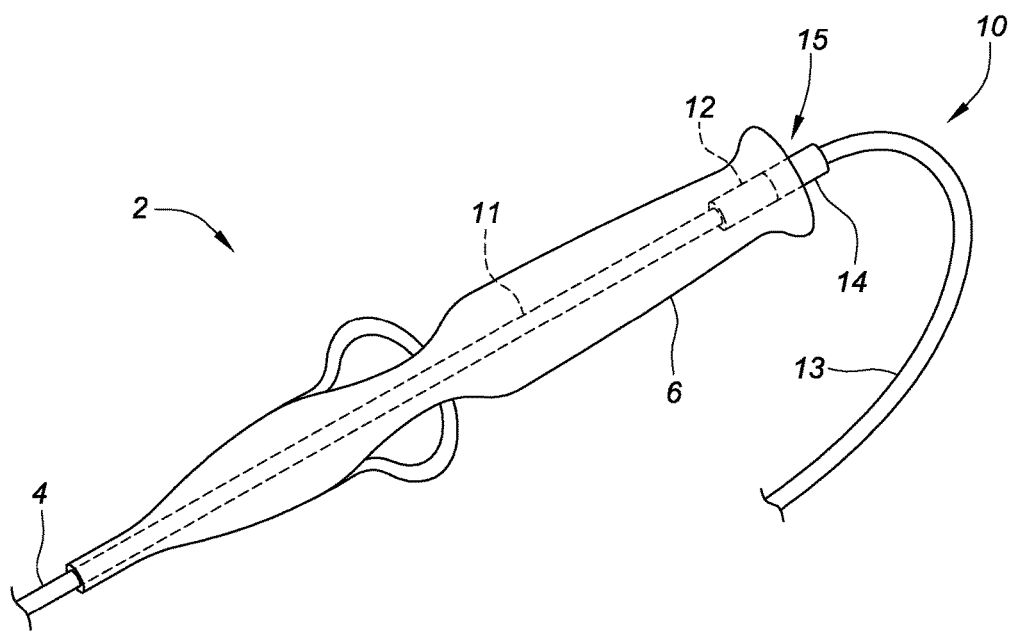
FIG. 2B is a cross-sectional view of another embodiment of a control handle for a catheter having a cable connection internal to the control handle.

FIG. 2A is a perspective view of a handle 6 for catheter 2. Cable 10 comprises a pigtail 11 extending from the handle 6 and a primary cable portion 13 extending to the system 18. The two portions of cable 10 are connected by connector 15, comprised of a pigtail connector 12 and a primary connector 14. Connector 15 facilitates the multiple electrical connections in the cable 10 between catheter 2 and the system 18. In other embodiments, such as shown in FIG. 2B, the connector 15 can be integrated into the handle 6. In the handle 6 shown in FIG. 2B, the pigtail connector 12 portion of connector 15 is disposed within the handle 6, arranged at the handle's proximal end. The mating primary connector 14, attached to the primary cable portion 13, attaches to the pigtail connector 12 at the end of the handle 6. In other embodiments, connector 15 may be positioned along other portions of handle 6, and may be embedded within handle 6 such that it is not accessible or able to be easily detached. In still other embodiments, connector 15 may be integrated into the structure of handle 6.

Figure 3A:
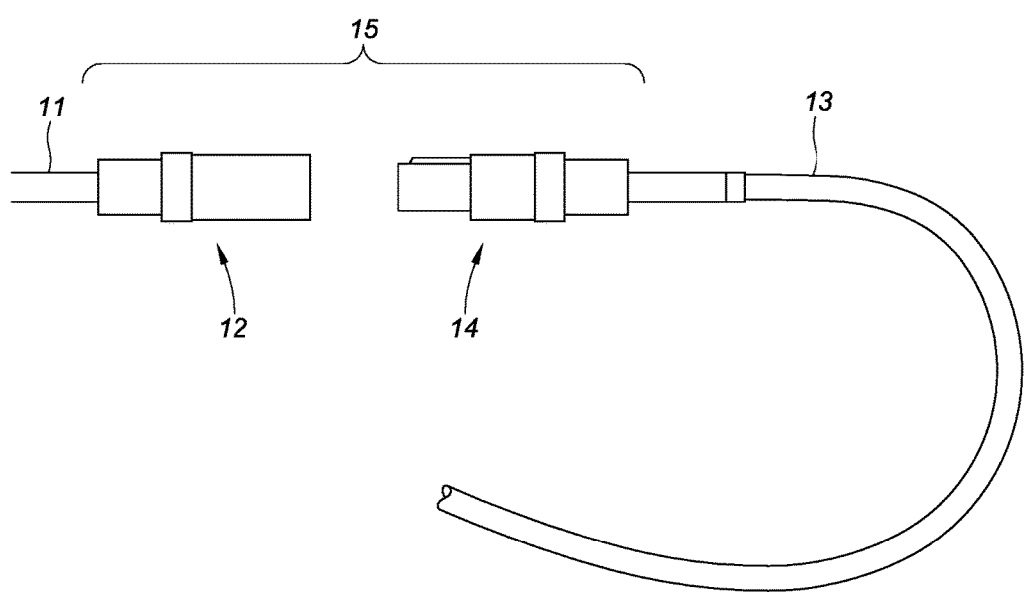
FIGS. 3A-3C illustrate various views of a prior art pin-to-socket connection system for a medical device.
Figure 3B:
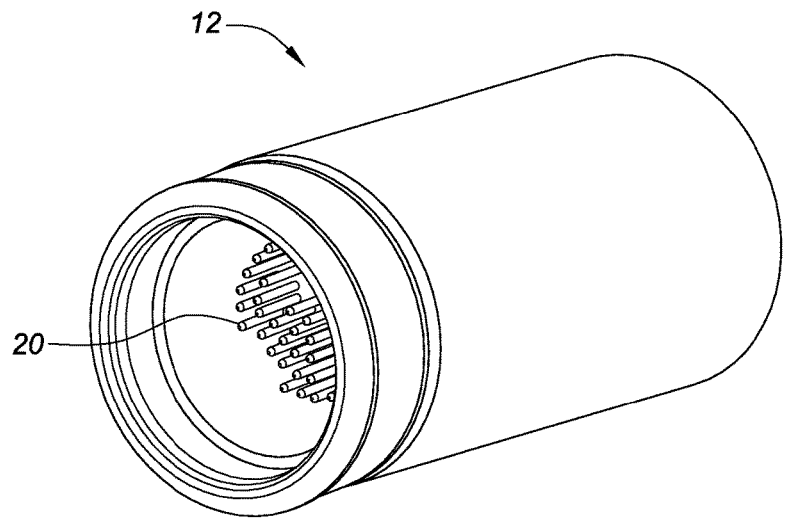
Figure 3C:
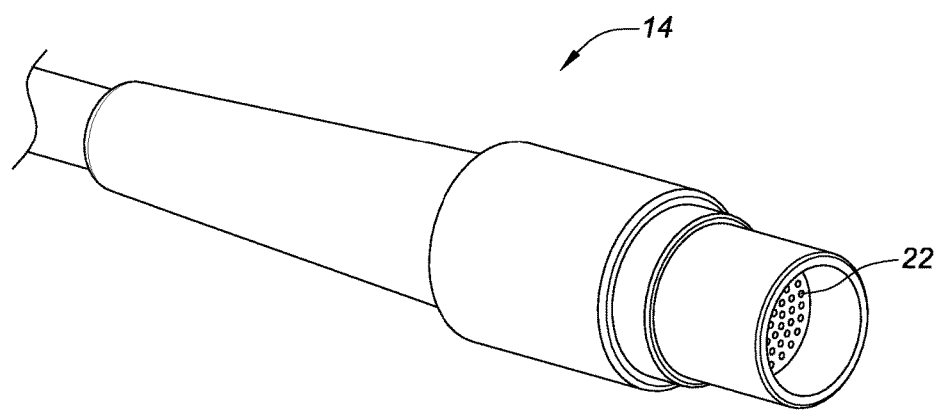

Many different types of connectors are used for the connector 15 in the prior art, with a common type being an electromechanical pin-to-socket type connector. FIGS. 3A, 3B and 3C depict a prior art connector 15 of the pin-to-socket type for connecting the parts 11, 13 of cable 10. The depicted prior art connector 15 comprises pigtail connector 12 and primary connector 14, which may be, for example, a male plug and a female receptacle, respectively.

As depicted in FIGS. 3B, 3C, a male plug connector 12 has a plurality of pins 20 while a female receptacle connector 14 has a plurality of sockets 22, the sockets 22 being configured to receive the pins 20 of the male plug connector 12. Each pin 20 and each socket 22 is electrically and mechanically connected or coupled to a respective lead (not shown) representing an electrical channel between the catheter 2 and the medical device system 18. The pins 20 of the male plug connector 12 and the sockets 22 of the female receptacle connector 14 are configured to correspond with each other when the two parts 12, 14 of the connector 15 are joined. The male plug connector 12 and female receptacle connector 14 may be keyed to ensure proper orientation.

The number of electrical channels between catheter 2 and system 18 carried by cable 10 having existing pin-to-socket connectors is dependent on the number of pins 20 and sockets 22 contained in the connector 15. An increase in the number of data channels requires an increase in the number of pins and sockets in the connector 15, which necessarily requires either smaller pins or a bigger connector. Since the pins 20 must be rigid enough to maintain adequate performance of the connector 15, there is a minimum size for the pins in order to ensure structural integrity. Thus, in order to increase the number of data channels in a pin-to-socket connector, the size of the connector must increase. For connectors located or integrated within the handle 6 of a catheter 2, this may also cause the handle 6 itself to be larger, which is not always desirable.

More data channels also requires more lead wires to be connected to each additional pin and socket in the connector. Traditional pin-to-socket connectors utilize soldering to connect the lead wires, which has a number of complications that make it difficult to add more wires. The difficulties include crowded and broken wires, shorts, solder flow, solder pool, solder bridges, and/or excessive solder. Furthermore, excess flux utilized during the soldering process may create noise, distorting the signal between a catheter 2 and a system 18.

The various embodiments described herein utilize unique flexible circuit based connector assemblies that allow for a high capacity of date channels while providing easier assembly, potentially avoiding some of the issues inherent in the prior art.

Figure 4:
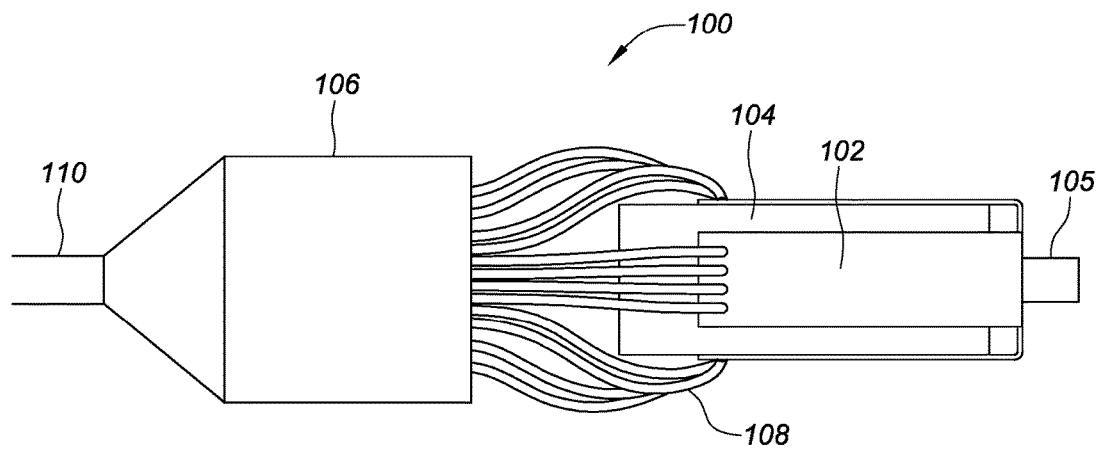
FIG. 4 is a view of the components of a connector assembly according to an embodiment of the present invention.

One embodiment of a high-capacity flexible circuit based connector is illustrated in FIG. 4, where it is shown in an exploded view. The connector assembly 100 of FIG. 4 includes a flexible circuit 102 shaped around an internal holder 104 having an engagement shaft 105 configured to mate with a corresponding portion of a second connector assembly, as described in detail below. An encasement 106 surrounds and protects the flexible circuit 102, but is shown in a "pulled-back" position for clarity. Electrical lead wires 108 connect to flexible circuit 102 and extend into cable 110. The internal holder 104 of the depicted embodiment is of a rectangular shape while the encasement 106 is of a cylindrical shape. Other embodiments may have an internal holder and/or encasement of any shape.

Figure 5:
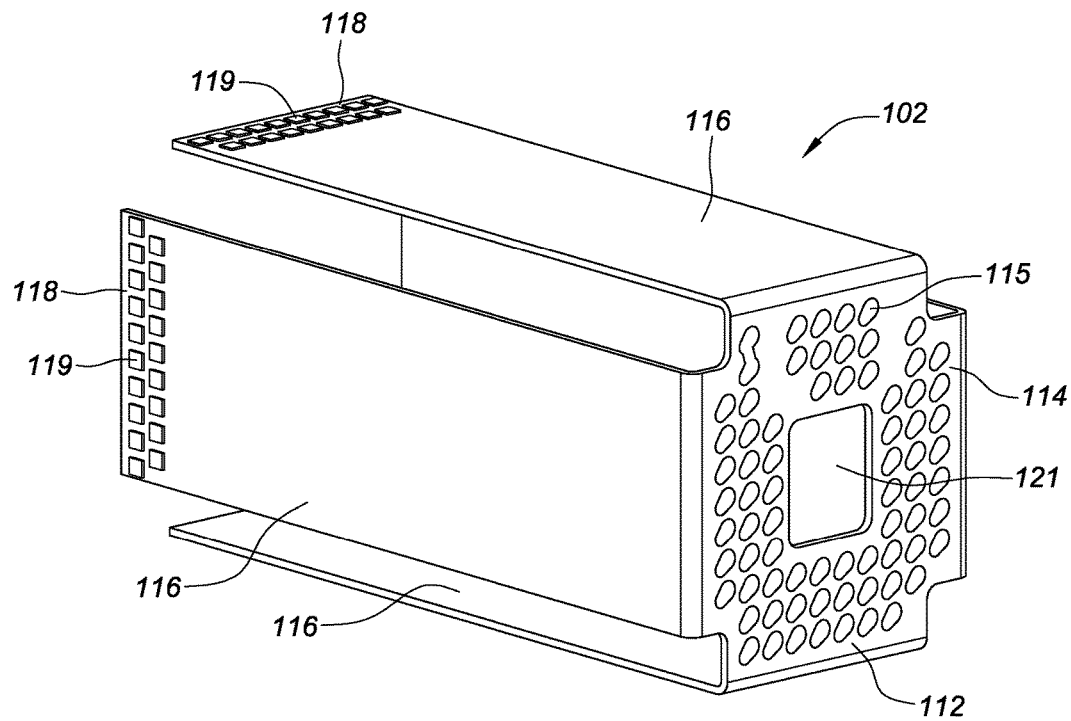
FIG. 5 is a perspective view of a flexible circuit of a connector assembly according to an embodiment of the present invention
Figure 6:
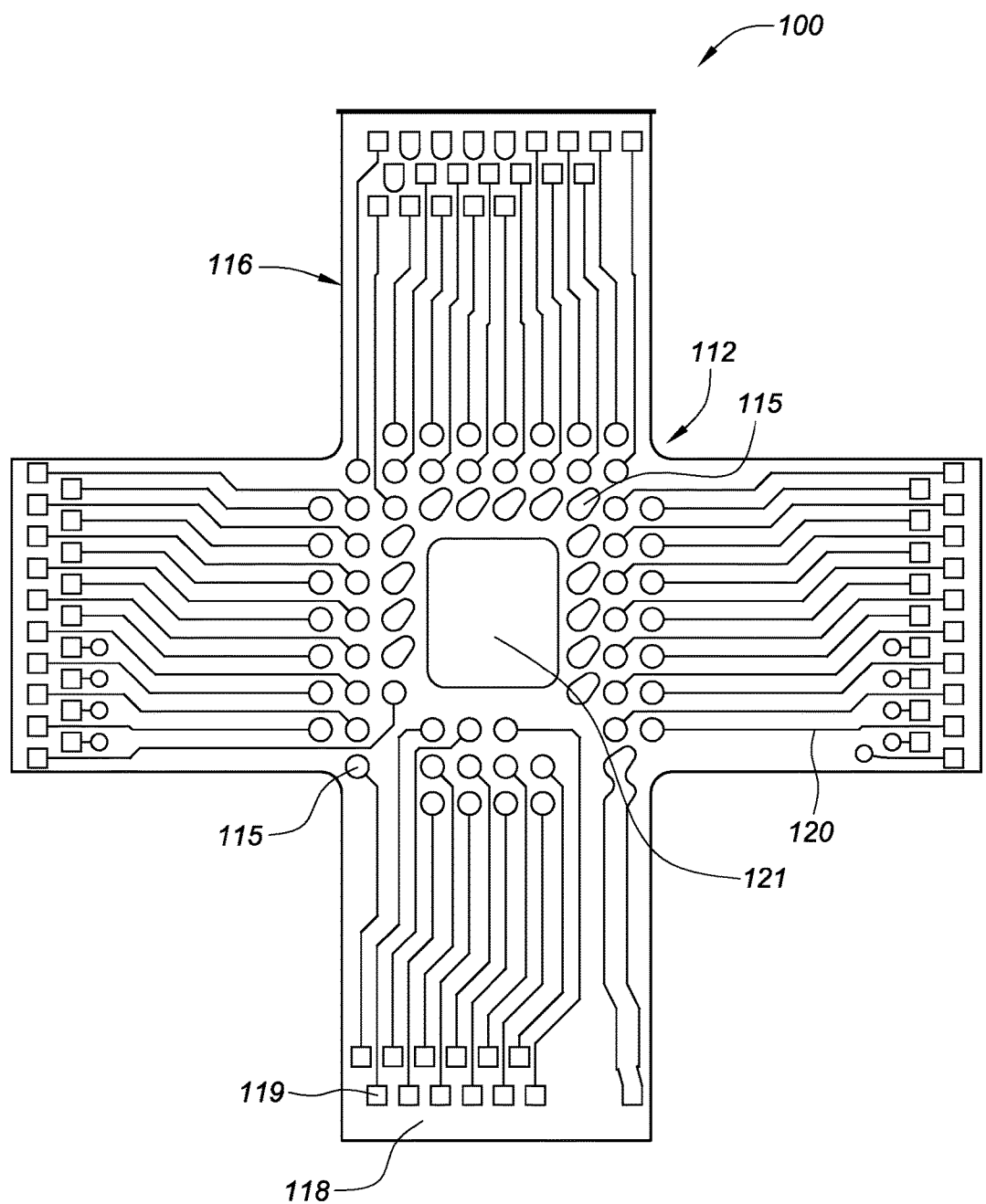
FIG. 6 is another view of the flexible circuit of FIG. 5.

The flexible circuit 102 of the connector assembly 100 of FIG. 4 is illustrated in FIG. 5, shaped to fit around the internal holder 104. The flexible circuit 102 comprises a base 112 having a high-density contact interface 114 located in a center portion and tab areas 116 extending from the base 112. The high-density contact interface 114 comprises a plurality of contact nodes 115 for creating an individual electrical connection. Each tab area has a high-density wiring interface 118 located at an end opposite the base 112. Each high-density wiring interface 118 comprises a plurality of contact pads 119 for connecting wire leads to the flexible circuit 102. As shown in FIG. 6, where the flexible circuit 102 is shown while flat, each contact node 115 in the high-density contact interface 114 is electrically connected to one of the contact pads 119 in any of the high-density wiring interfaces 118 by electrical pathways 120. Thus, an electrical path is created between each lead wire and one of the contact nodes 115 on the high-density contact interface 114. The flexible circuit 102 includes an opening 121 configured to allow the passage of the engagement shaft 105 of the internal holder 104 through the flexible circuit 102. While the flexible circuit 102 is depicted in a cross-shape with four tab areas 116 extending from the base 112, other shapes and more or less tabs are contemplated.

Figure 7:
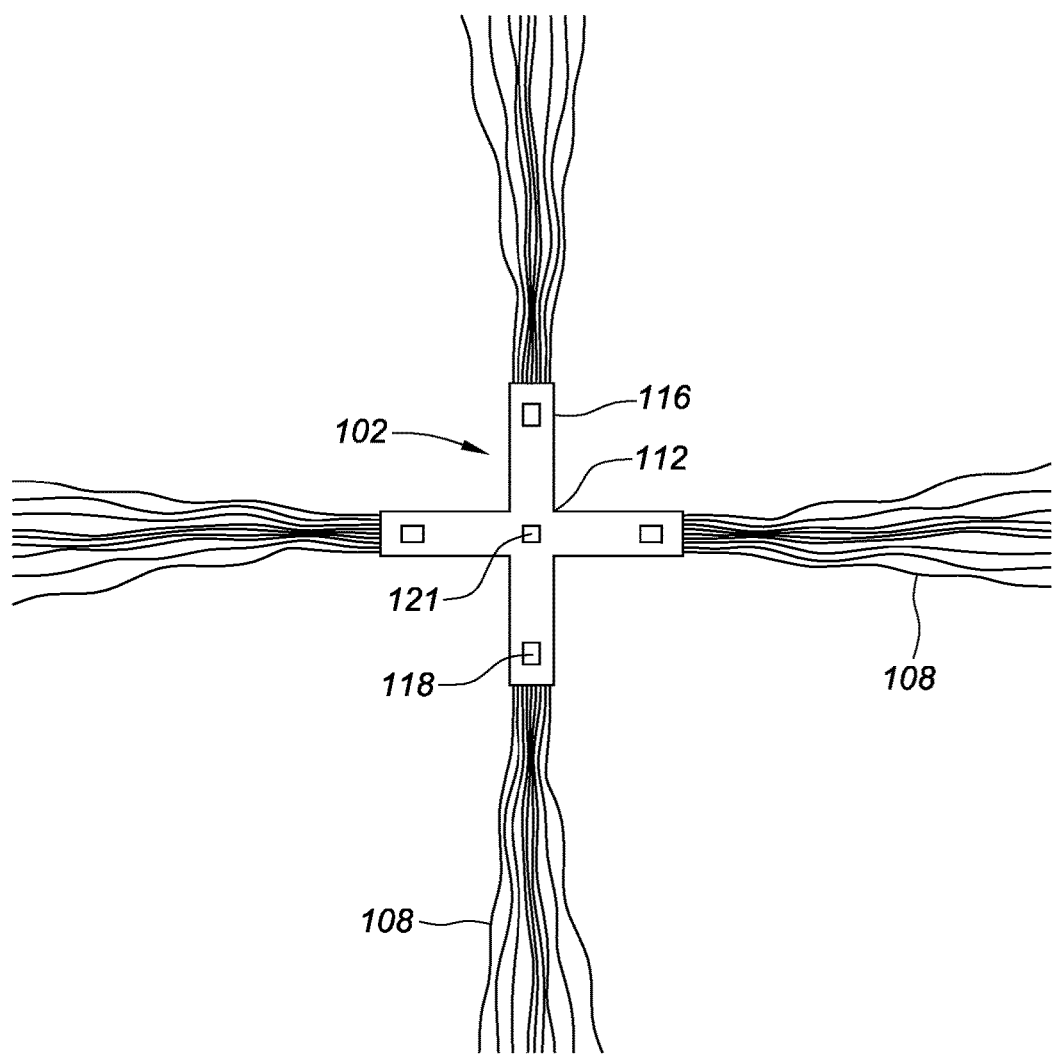
FIG. 7 illustrates the flexible circuit of FIG. 6 with wire leads connected thereto.

FIG. 7 depicts the flat flexible circuit 102 with lead wires 108 extending from the wiring interface 118 of each tab area 116. Having the connection pads for the lead wires spread out as shown in FIG. 7 provides an easier manufacturing process with less complications due to overcrowding, as known with prior art pin-to-socket connectors.

After the lead wires 108 are connected to the wiring interface, the flexible circuit 102 is folded into shape for mounting onto the internal holder 104, as shown in FIGS. 4, 5.

Figure 8A:
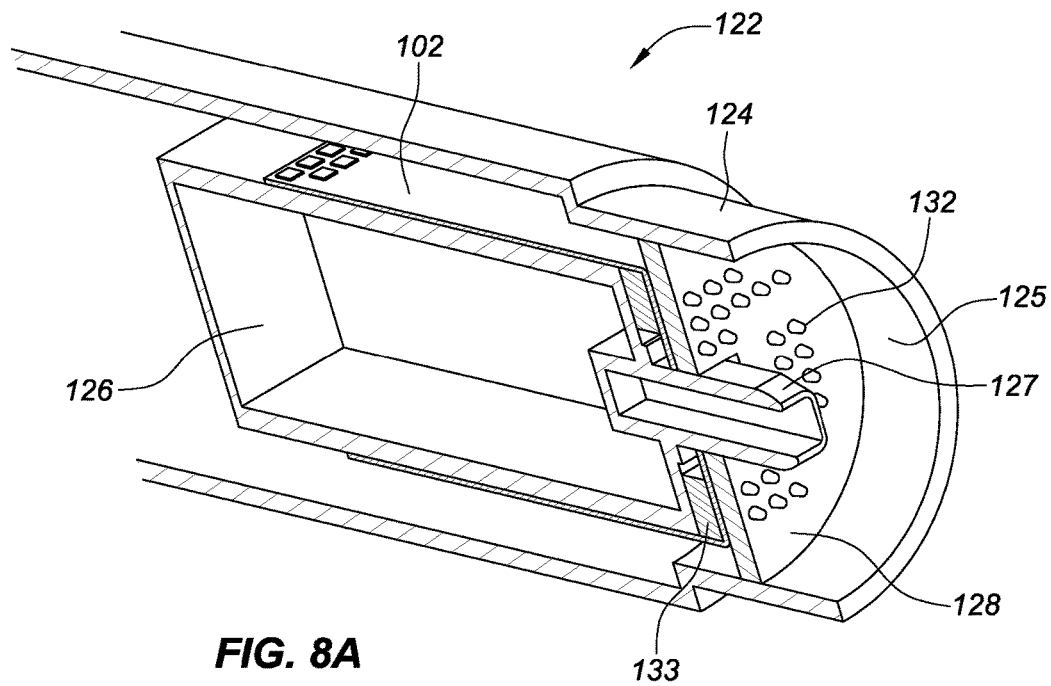
FIGS. 8A, 8B are perspective views of two halves of a connector assembly according to an embodiment of the present invention utilizing the flexible circuit of FIGS. 5-7.
Figure 8B:
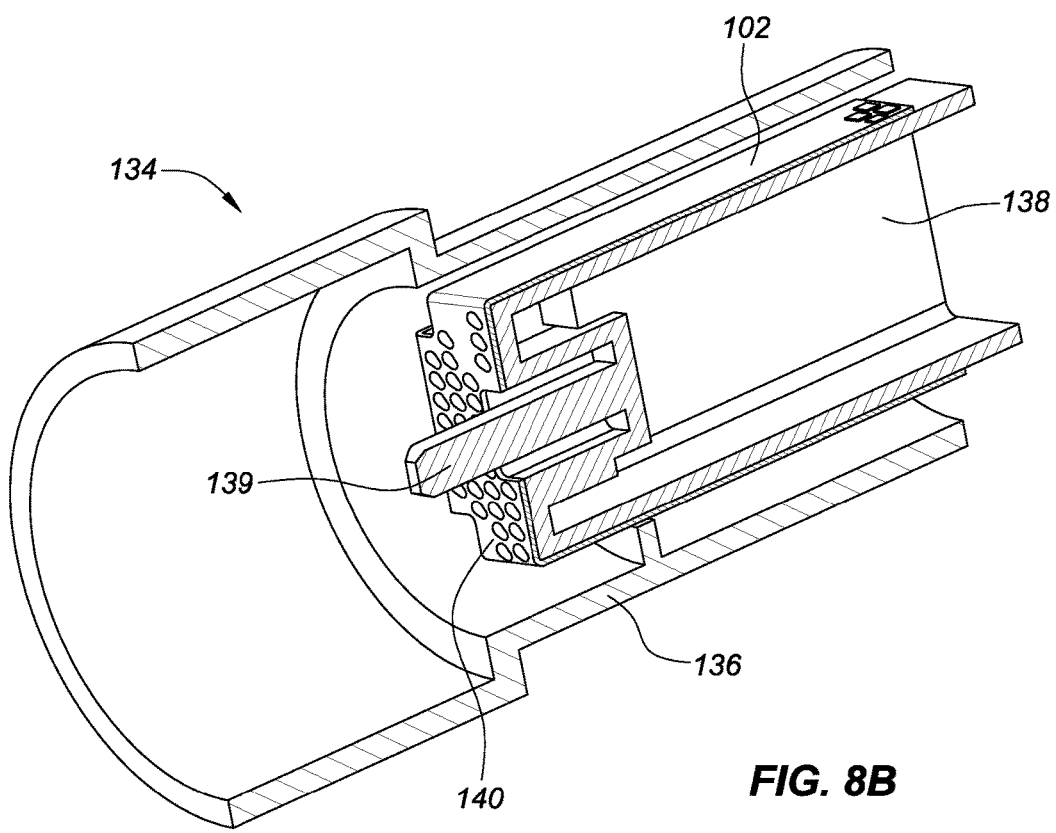

The high-capacity flexible circuit based connector assembly 100 may be paired with a matching connector assembly to make a cable connector that replaces a common pin-to-socket connector and is able to provide a higher capacity than such a prior art connector. FIGS. 8A, 8B illustrate such an embodiment where each portion of a cable connector utilizes the flexible circuit 102. A male connector assembly 122 comprises a flexible circuit 102 configured around a first internal holder 126 having a hollow shaft 127. The first internal holder 126 and flexible circuit 102 are arranged within an encasement 124, the encasement 124 having an opening 125 at one end for engaging with a matching portion of a cable connector. A female connector assembly 134, as illustrated in FIG. 8B, comprises a flexible circuit 102 configured around a second internal holder 138 having a shaft 139 extending from the internal holder 138. Shaft 139 is configured to slidably engage within the hollow shaft 137 of male connector assembly 122. The second internal holder 138 and flexible circuit 102 are arranged within an encasement 136. Encasements 124 and 136 are configured to lockably engage each other.

Connector assembly 122 further comprises a conductor layer 128 located inside the encasement 124 and configured to contact the high-density contact interface 131 of the flexible circuit 102. The conductor layer 128 has a plurality of conductor nodes 132 spanning both sides of the conductor layer 128, with the conductor nodes 132 corresponding to the plurality of contact nodes 115 on the flexible circuit 102. The conductor nodes 132 provide an electrical connection between the contact nodes 115 of the flexible circuits 102 when the male and female connector assemblies 122, 134 are engaged. Other embodiments may not include a layer of conductor layer 128 and may provide for direct connection of the flexible circuit contact interfaces.

The engagement of the conductor layer 128 with the two flexible circuits 102 can be enhanced with a spring force, pressure force, mechanical connection or other means to ensure contact between the conducting nodes. In the embodiment of the male connector assembly 122, a spring material 133 is arranged between the base 112 of the flexible circuit 102 and the first internal holder 126.

Figure 9:
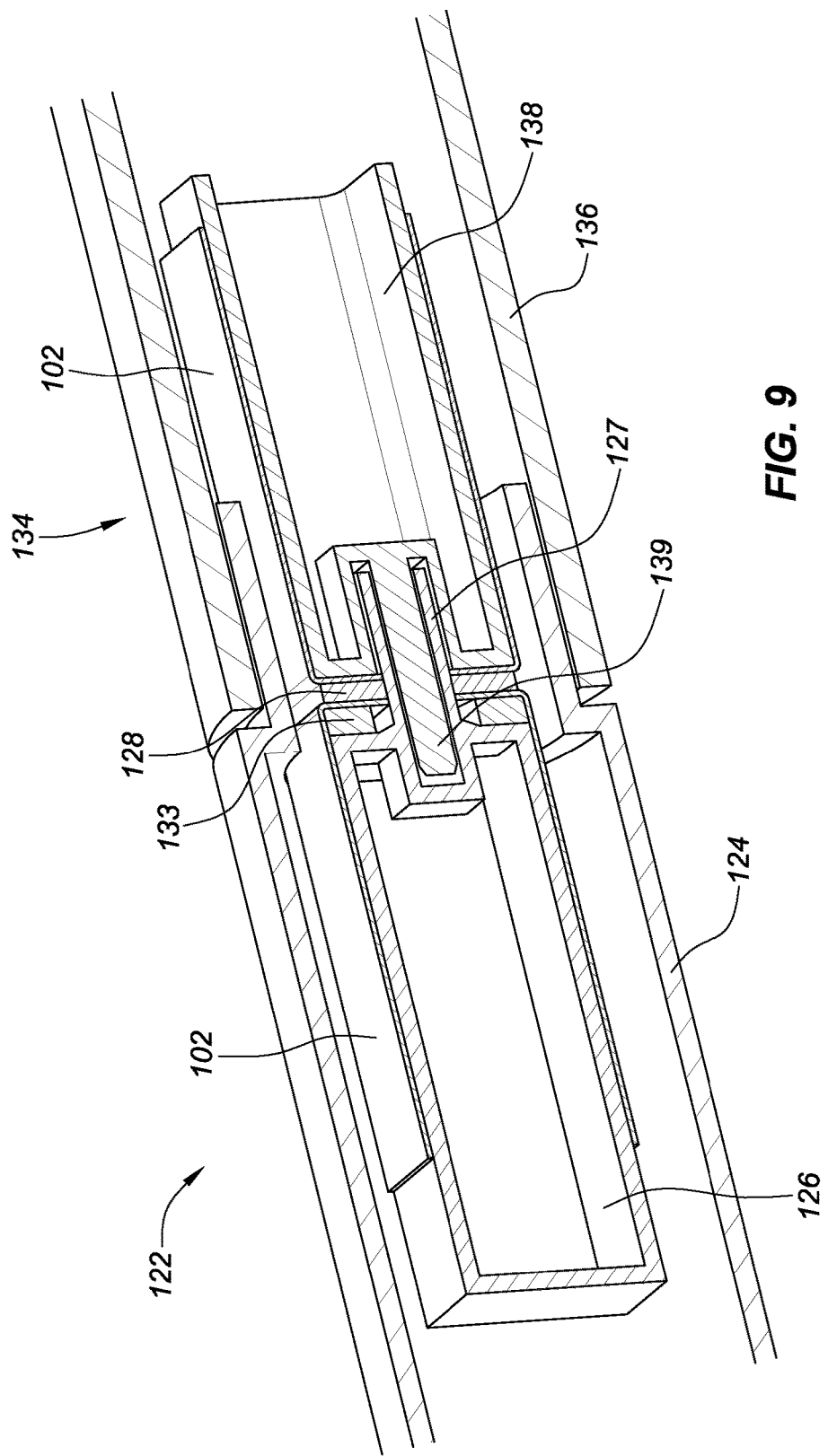
FIG. 9 is a cross-sectional view of the two halves of the connector assembly of FIGS. 8A, 8B joined together.

FIG. 9 shows a simplified cross-sectional view of the connector assemblies 122, 134 engaged together. The assemblies 122, 134 can employ various mechanical means to ensure a secure connection. The male encasement 124 fits into the female encasement 136 while shaft 139 of the second internal holder 138 fits into the hollow shaft 127 of the first internal holder 126. Electrical connection between the two flexible circuits 102 is provided by the conductor layer 128, with spring material 133 providing a pressure force to maintain the contact of the flexible circuits 102 and the conductor layer 128.

Figure 10A:
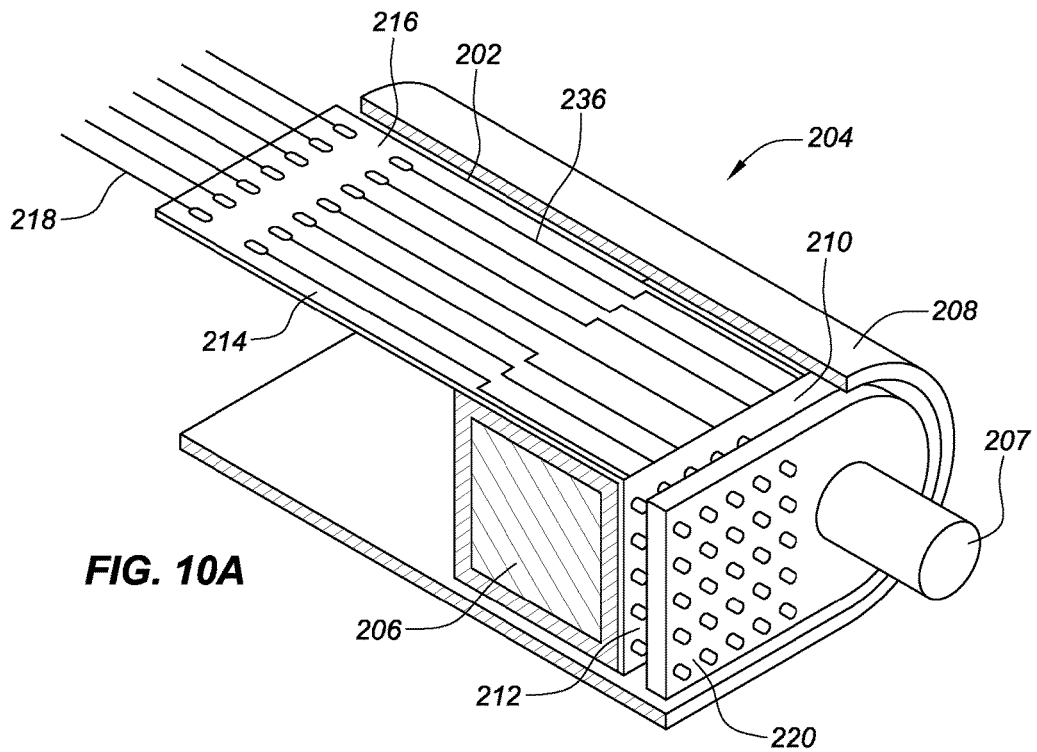
FIGS. 10A, 10B are cross-sectional views of two halves of a stacking connector assembly according to an embodiment of the present invention.
Figure 10B:
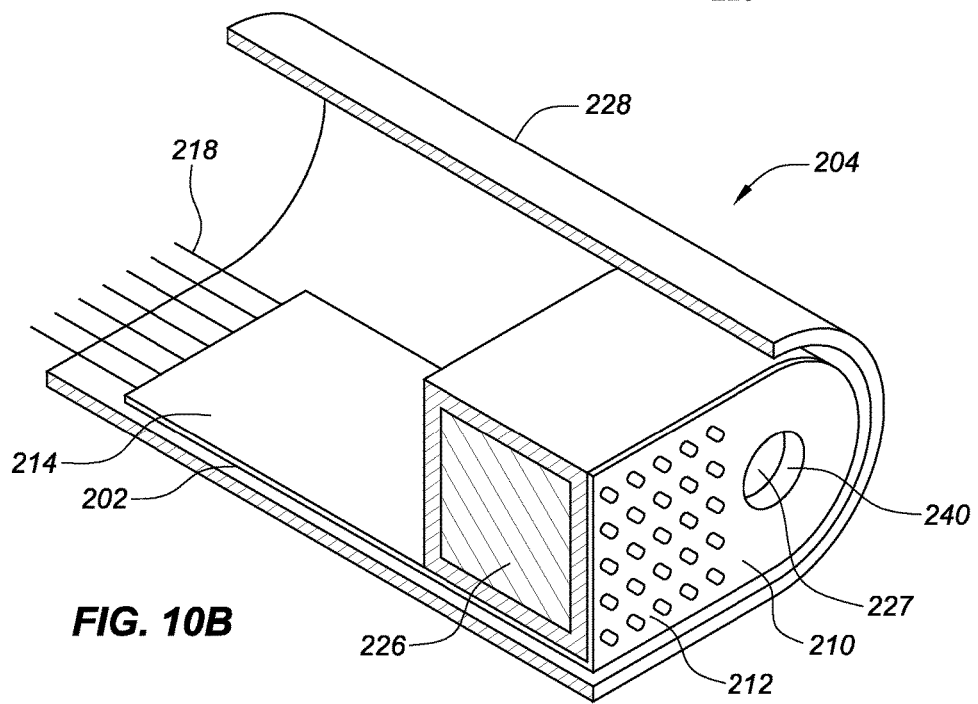

The embodiments described above all depict connector assemblies having round or cylindrical shape, but other shapes are possible and contemplated by this disclosure. Another common connector type that may incorporate a flexible circuit based connector as disclosed herein is a C-stack connector. FIGS. 10A, 10B depict cross-sectional views of two-halves, connector portions 204, 224, of such a connector type, with each half having a high-density flexible circuit 202. Connector portion 204 includes a first internal holder 205 which is configured to hold a flexible circuit 202. Encasement 208 surrounds and protects the flexible circuit 202. Connector portion 204 further includes a conductor layer 220, which, like conductor layer 128, facilitates electrical connection between the high-density contact interface 212 on the flexible circuits 202. A conductor layer may or may not be utilized in other embodiments. Connector portion 224 includes second internal holder 226 configured to hold a flexible circuit 202. Encasement 228 surrounds and protects the flexible circuit 202 in connector portion 224.

First internal holder 206 includes peg 207 while second internal holder 226 includes aperture 227 configured to accept peg 207. The peg 207 and aperture 227 facilitate the connection and alignment of connector portions 204 and 224. In the embodiments of FIGS. 10A, 10B, only half of the connector portions 204, 224 are shown. The halves not shown are symmetrical to the shown half in this embodiment. In other embodiments, the connector portions may be asymmetrical.

Figure 11:
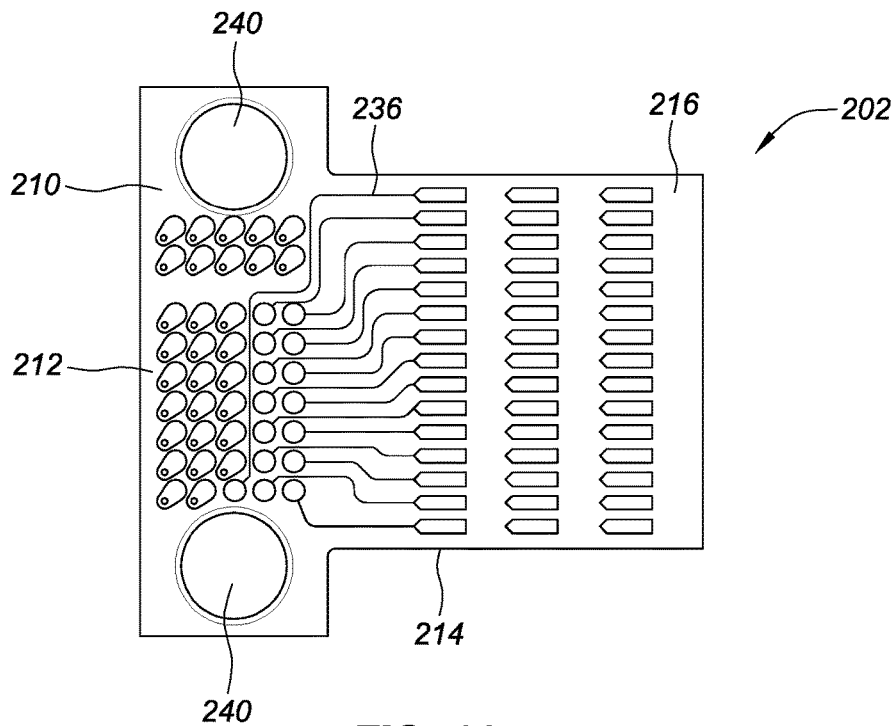
FIG. 11 illustrates one embodiment of a flexible circuit for use in the stacking connector of FIGS. 10, 10B.

FIG. 11 shows a plan view of flexible circuit 202 used in connector portions 204, 224. Flexible circuit 202 comprises a base area 210 and a tab area 214. The base area 210 contains the high-density contact interface 212 while the tab area 214 contains a high-density wiring interface 216. Electrical pathways 236 provide electrical connections between the high-density contact interface 212 and the high-density wiring interface 216. As shown in FIGS. 10A, 10B, lead wires 218 are connected to the flexible circuit 202 at the high-density wiring interface 216. Base area 210 is configured to engage a top surface of either internal holders 206, 226, while tab area 214 is configured to be folded perpendicular to the base area 210 and engage a side surface of either internal holders 206, 226. Flexible circuit 202 further includes apertures 240 configured to accept pegs 207 of the first internal holder 206.

Figure 12:
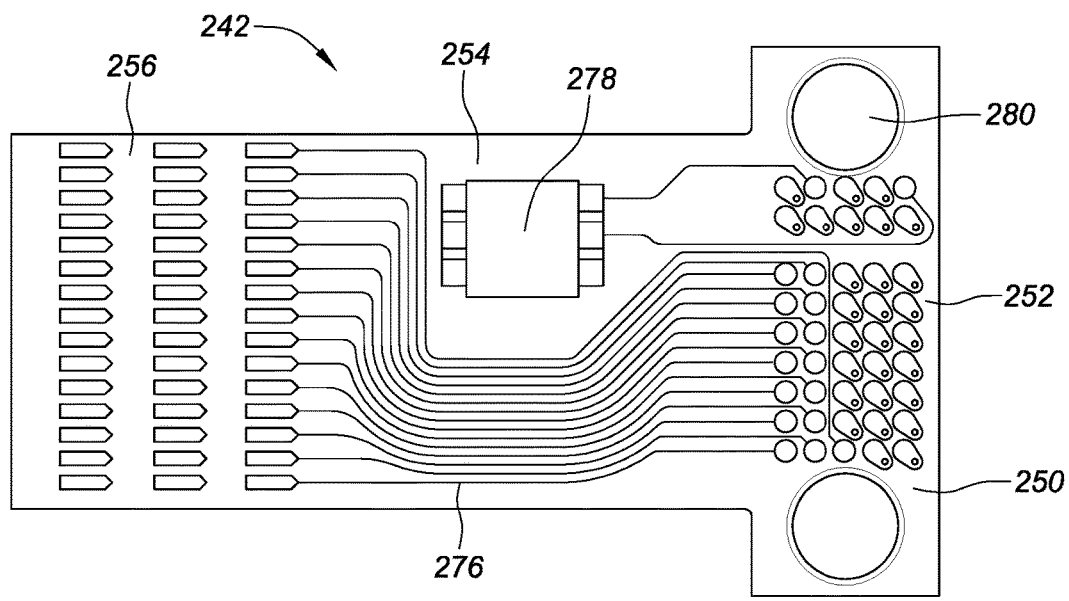
FIG. 12 illustrates another embodiment of a flexible circuit for use in the stacking connector of FIGS. 10A, 10B.

Another embodiment of a flexible circuit that may be used in the connector assemblies of FIGS. 10A, 10B is illustrated in plan view in FIG. 12. There, flexible circuit 242 is similar to flexible circuit 202, having a base area 250 with a high-density contact interface 252 connected by electrical pathways 276 to a high-density wiring interface 256 on a tab area 254. Apertures 280 are configured to accept pegs 207. Flexible circuit 242 includes space for one or more pre-mounted components 278, such as logic components, memory components, and/or switches. As an example, a pre-mounted memory component may include EEPROM. Adding space for pre-mounted components may also be applied to other flexible circuits described herein, such as flexible circuit 102.

The flexible circuit based connectors disclosed herein have so far been described in connectors having flexible circuits on each side of the connection and with physical connections between contact pads. Flexible circuit based connectors can also be used as an adapter to interface with existing connectors, such as pin-to-socket connectors, or configured to resemble a current common connector, such as a pin-to-socket connector, on both sides of the connection. Thus, a flexible circuit based connector can provide backwards compatibility with existing connectors and/or a familiar configuration to users.

Figure 13:
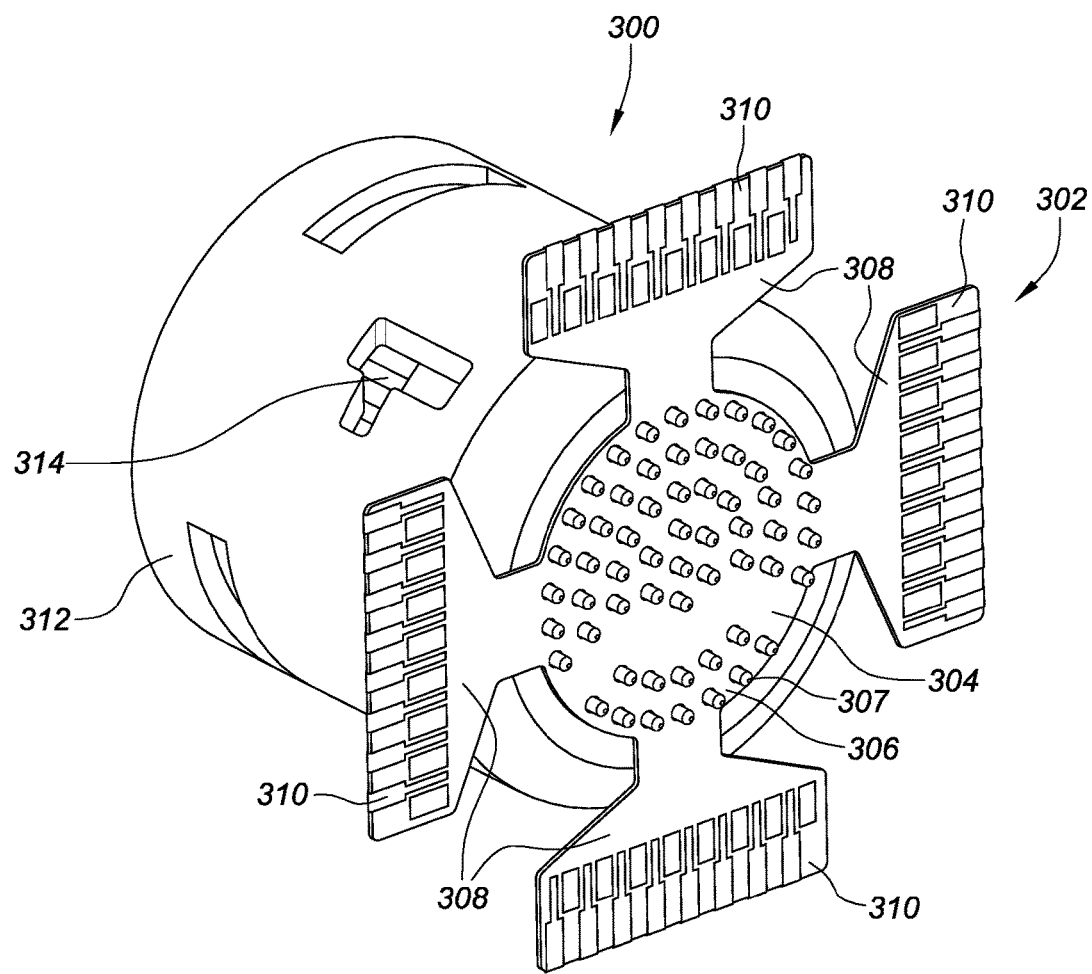
FIG. 13 is a perspective view of connector assembly according to another embodiment of the present invention.

An embodiment of a flexible circuit based adapter for a conventional pin connector is shown in FIG. 13 for connecting to with an existing socket connector. The adaptor assembly 300 comprises flexible circuit 302 having a base area 304 and tab areas 308. The base area 304 includes a high-density contact interface 306 having a plurality of contact nodes 307 extending through the flexible circuit 302 to the opposite side (not shown). Each tab 308 includes a high-density wiring interface 310. A plurality of pins 314 are electrically connected to each of the contact nodes 307 on the opposite side (not shown) of the base area 304 of the flexible circuit 302. A cover 312 surrounds the pins 314 and may provide mechanical means for connecting to a matching socket connector. In another embodiment, adapter assembly 300 may include sockets instead of pins 314 and may connect to a matching pin connector. In either embodiment, the matching connector may be a conventional socket or pin connector, respectively. Alternatively, both connectors could utilize flexible circuit 302, with one incorporating pins 314 as shown in FIG. 13, and the other incorporating sockets. In this embodiment, the benefits of the disclosed high-capacity flexible circuit based connector can be achieved while providing users with a familiar pin-to-socket interface.

Figure 14:
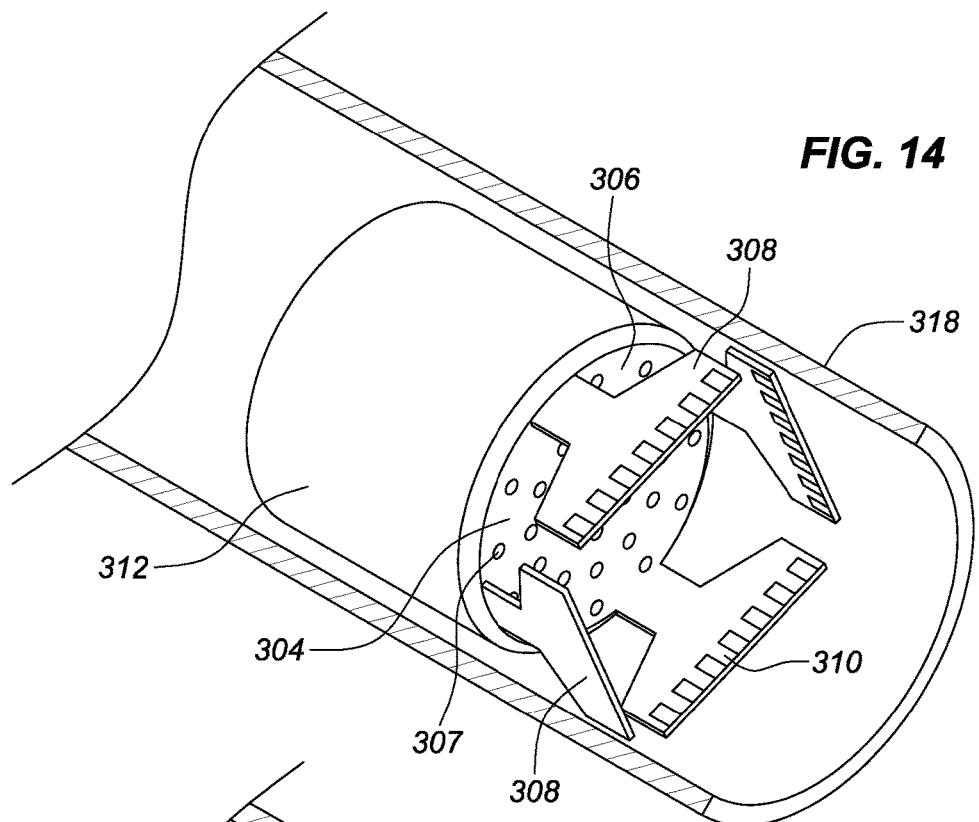
FIG. 14 show another view of the connector assembly of FIG. 13 utilized inside a housing.
Figure 15:
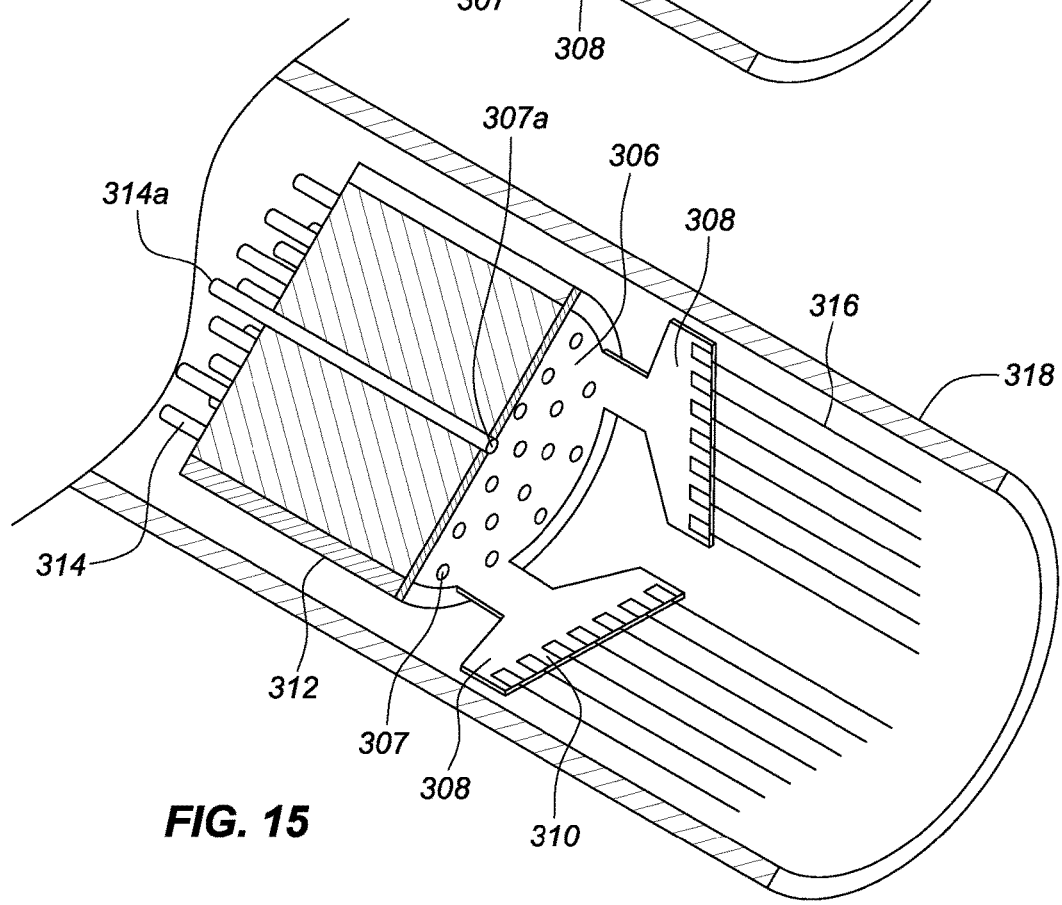
FIG. 15 is a cross-sectional view of the connector assembly of FIG. 14 having lead wires extending from a flexible circuit.

In FIGS. 14, 15 adapter assembly 300 is shown within a cross-section of an encasement 318. In some embodiments, the encasement 318 may be an outer enclosure such that the adapter assembly 300 is affixed to the end of a medical device cable, similar to the embodiment shown in FIG. 2A. In other embodiments the adapter assembly 300 can be integrated within a handle of a catheter such as shown in FIG. 2A. In still further embodiments, the encasement 318 may further be configured to provide magnetic field shielding to the lead wires 316. For example, encasement 318 may comprise a connector shield, such as disclosed in U.S. patent application Ser. No. 15/392,812, filed on Dec. 28, 2016, entitled Connector Shield For Sensor Enabled Medical Devices, the entire disclosure of which is hereby incorporated by reference.

In the adapter assembly 300 of FIGS. 14, 15, tab areas 308 are folded perpendicular to the base area 304 to facilitate the fit of adapter assembly 300 inside encasement 318. Electrical pathways connect the plurality of contact nodes 307 to the plurality of pins 314, as shown by the example connection between node 307a and pin 314a. In another embodiment, instead of the plurality of pins 314, the adapter assembly 300 may have a plurality of sockets, which in turn would be connected by electrical pathways to the plurality of contact nodes 307.

Lead wires 316 are shown connected to the high-density wiring interfaces 310 on each of the tab areas 308. In other embodiments, instead of lead wires, the high-density wiring interfaces 310 may be directly connected to a flexible circuit that carries the electrical signals from the adaptor assembly 300 to the one or more electrodes mounted in or on the distal portion 8 of the elongate shaft 4 of a catheter 2.

Figure 16:
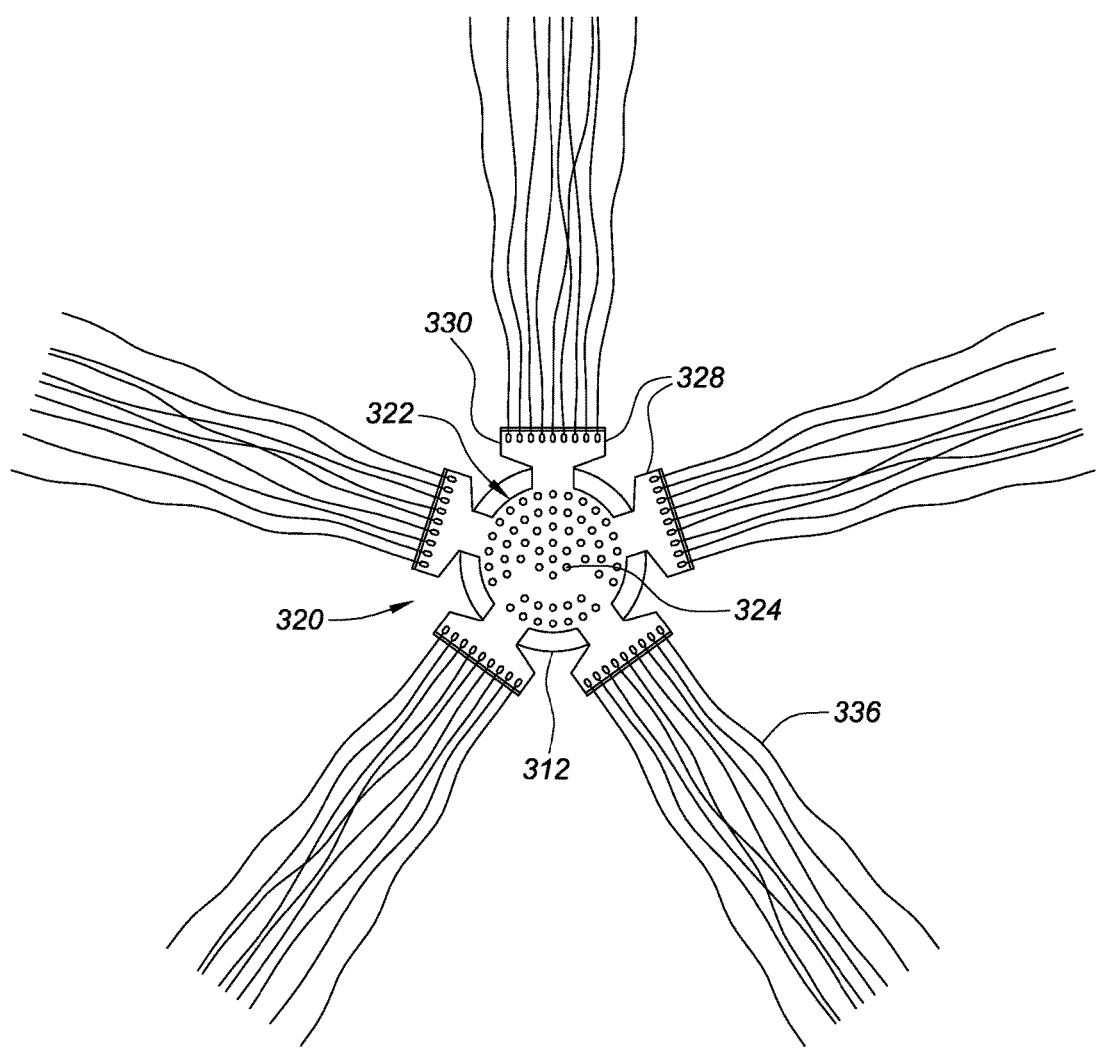
FIG. 16 is a bottom view of a connector assembly according to another embodiment of the present invention, having lead wires extending from a flexible circuit.

Flexible circuit 302 is shown having four tab areas 308 in the embodiment of FIGS. 13-15. In other embodiments, flexible circuit 302 may have less than four tab areas 308 or more than four tab areas 308. FIG. 16 shows an adapter assembly 320 with a flexible circuit 322 having five tab areas 328 extending from base 324. Lead wires 336 are attached to high-density wiring interfaces 330 located on each of tab areas 328.

Although several embodiments of this invention have been described above with a certain degree of particularity, those skilled in the art could make numerous alterations to the disclosed embodiments without departing from the spirit or scope of this invention. For example, the flexible circuit and the flexible tabs may take any shape or may be folded, bent, curved, or manipulated to fit into a variety of encasements and/or cables.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electrical connection apparatus for a medical device, the electrical connection apparatus comprising:
   a flexible circuit comprising:
      a base area;
      at least one tab area extending from the base area, the tab area being configured to be folded substantially perpendicular to the base area;
      a plurality of contact nodes disposed on the base area;
      a plurality of contact pads disposed on the at least one tab area at an end away from the base area; and
      a plurality of electrical pathways individually connecting each of the contact nodes to one of the contact pads;
   an internal holder comprised of a face area and at least one side perpendicular to the face area, wherein the base area of the flexible circuit is disposed on the face area of the internal holder and the at least one tab area is disposed on the at least one side when folded;
   a plurality of lead wires individually attached to the plurality of contact pads on the at least one tab area of the flexible circuit; and
   an encasement surrounding the flexible circuit and internal holder and having an opening at one end, wherein the encasement is configured to be attached to a second electrical connection apparatus and wherein the opening is configured to allow electrical connections between the plurality of contact nodes disposed on the base area of the flexible circuit and the second electrical connection apparatus.

2. The electrical connection apparatus of claim 1, further comprising:
   at least one aperture located on the face area of the internal holder; and
   at least one aperture located in the base area of the flexible circuit aligned with and having substantially the same size and cross-section as the aperture on the face area of the internal holder;
   wherein the at least one aperture on the internal holder and the at least one aperture on the flexible circuit are configured to accept a portion of the second electrical connection apparatus.

3. The electrical connection apparatus of claim 1, further comprising a pressure means configured to maintain physical contact between the contact nodes on the base of the flexible circuit and the second electrical connector apparatus.

4. The electrical connection apparatus of claim 3, wherein the pressure means comprises a spring.

5. The electrical connection apparatus of claim 4, wherein the spring is a material disposed between the face area of the internal holder and the base area of the flexible circuit.

6. The electrical connection apparatus of claim 1, further comprising a conductor layer disposed on top of the base area of the flexible circuit, the conductor layer having a plurality of conducting nodes extending through opposite sides of the conductor layer, the conducting nodes on a first side of the conductor layer being in contact with the contact nodes on the flexible circuit.

7. The electrical connection apparatus of claim 6, wherein the conductor layer is comprised of a compressible material and is configured to maintain contact between the conducting nodes and the contact nodes on the flexible circuit when compressed.

8. The electrical connection apparatus of claim 1, further comprising:
   at least one shaft attached to the internal holder and extending substantially perpendicular from the face area of the internal holder; and
   at least one aperture located in the base area of the flexible circuit, the aperture configured to accept the shaft,
   wherein the shaft is configured to facilitate connection of the electrical connection apparatus to the second electrical connection apparatus.

9. The electrical connection apparatus of claim 8, wherein the shaft is hollow and is configured to receive a portion of second electrical connection apparatus.

10. The electrical connection apparatus of claim 1, wherein the flexible circuit comprises one or more electronic components mounted on its surface.

11. The electrical connection apparatus of claim 10, wherein the one or more electronic components are comprised of at least one of a logic component, a memory component, and a switch.

12. A electrical connection adapter, the adapter comprising:
   a cover having an opening at one end, the opening being configured to connect to a second electrical connection;
   a flexible circuit attached to the cover at an end opposite the opening, the flexible circuit comprising:
      a base area adjacent to the cover;

at least one tab area extending from the base area, the tab area configured to be folded substantially perpendicular to the base area and away from the cover;

a plurality of contact nodes disposed on the base area, the contact nodes extending through the flexible circuit;

a plurality of contact pads disposed on the at least one tab area at an end away from the base area; and a plurality of electrical pathways individually connecting each of the contact nodes to one of the contact pads; and a plurality of electrical connectors disposed within the cover, the electrical connectors being individually electrically and mechanically attached to the plurality of contact nodes on the base area of the flexible circuit.

13. The electrical connection adapter of claim 12, wherein the plurality of electrical connectors are pins configured to connect to a socket-type connector.

14. The electrical connection adapter of claim 12, wherein the plurality of electrical connectors are sockets configured to connect to a pin-type connector.

15. The electrical connection adapter of claim 12 further comprising an encasement surrounding the cover and the flexible circuit and configured to provide mechanical connection with a second electrical connection.

16. The electrical connection adapter of claim 12 further comprising a plurality of lead wires individually attached to the plurality of contact pads on the at least one tab area of the flexible circuit.

17. An electrical connection adapter, the adapter comprising:

a hollow connector body having an open end and a closed end opposite the open end;

a flexible circuit having a base area, the base area being attached to the connector body on the outside of the closed end, the flexible circuit further comprising:

at least one tab area extending from the base area, the tab area configured to be folded substantially perpendicular to the base area and away from the connector body;

a plurality of contact nodes disposed on the base area, the contact nodes extending through the flexible circuit;

a plurality of contact pads disposed on the at least one tab area at an end away from the base area; and a plurality of electrical pathways individually connecting each of the contact nodes to one of the contact pads; and a plurality of electrical connectors disposed within the connector body and extending through the closed end of the connector body, the electrical connectors being individually electrically and mechanically attached to the plurality of contact nodes on the base area of the flexible circuit and terminating near the open end of the connector body.

* * * * *